United States Patent [19]

Helms et al.

[11] Patent Number: 4,947,129

[45] Date of Patent: Aug. 7, 1990

[54] PETROLEUM STREAM MICROWAVE WATERCUT MONITOR

[75] Inventors: David A. Helms; John D. Marrelli, both of Houston, Tex.

[73] Assignee: Texaco Inc., White Plains, N.Y.

[21] Appl. No.: 280,079

[22] Filed: Dec. 5, 1988

[51] Int. Cl.$^5$ .......................................... G01N 22/04
[52] U.S. Cl. ................................... 324/640; 324/641; 333/245; 333/260
[58] Field of Search ...................... 324/58.5 A, 58.5 R, 324/58 A, 58 R; 73/61.1 R; 333/24.2, 24 C, 1.1, 248, 245, 260

[56] References Cited

U.S. PATENT DOCUMENTS

| | | | |
|---|---|---|---|
| 4,242,655 | 12/1980 | Carlson et al. | 333/260 X |
| 4,399,419 | 8/1983 | Dobrovolny | 333/245 X |
| 4,499,418 | 2/1985 | Helms et al. | 324/58.5 A |
| 4,727,311 | 2/1988 | Walker | 324/58.5 A |

Primary Examiner—Gerard R. Strecker
Assistant Examiner—Robert W. Mueller
Attorney, Agent, or Firm—Robert A. Kulason; James J. O'Loughlin; Ronald G. Gillespie

[57] ABSTRACT

The petroleum stream watercut monitor includes a test cell having a petroleum stream flowing through it. A microwave transmitter provides microwave energy through an antenna through an isolator. The antenna irradiates the test cell with the microwave energy so that the microwave energy enters the test cell and is reflected from the petroleum stream back to the antenna. A circulator connected to the isolator connects the transmitter to the isolator means and provides microwave energy to the antenna through the isolator and receives from the antenna again through the isolator the reflected microwave energy. An indicator provides an indication of the watercut of the petroleum stream in accordance with the phase difference between the transmitted microwave energy and the test microwave energy.

8 Claims, 2 Drawing Sheets

PETROLEUM STREAM MICROWAVE WATERCUT MONITOR

BACKGROUND OF THE INVENTION

Field of the Invention

The present invention-relates to petroleum stream monitors in general and, more particularly, to petroleum stream watercut monitors.

SUMMARY OF THE INVENTION

The petroleum stream watercut monitor includes a test cell having a petroleum stream flowing through it. A microwave transmitter provides microwave energy through an antenna through an isolator. The antenna irradiates the test cell with the microwave energy so that the microwave energy enters the test cell and is reflected from the petroleum stream back to the antenna. A circulator connected to the isolator connects the transmitter to the isolator means and provides microwave energy to the antenna through the isolator and receives from the antenna again through the isolator the reflected microwave energy. An indicator provides an indication of the watercut of the petroleum stream in accordance with the phase difference between the transmitted microwave energy and the test microwave energy.

The objects and advantages of the invention will appear more fully hereinafter, from a consideration of the detailed description which follows, taken together with the accompanying drawing where one embodiment is illustrated by way of example. It is to be expressly understood, however, that the drawing is for illustrative purposes only, and it is not to be construed as defining the limits of the invention.

DESCRIPTION OF THE INVENTION

Figure 1:
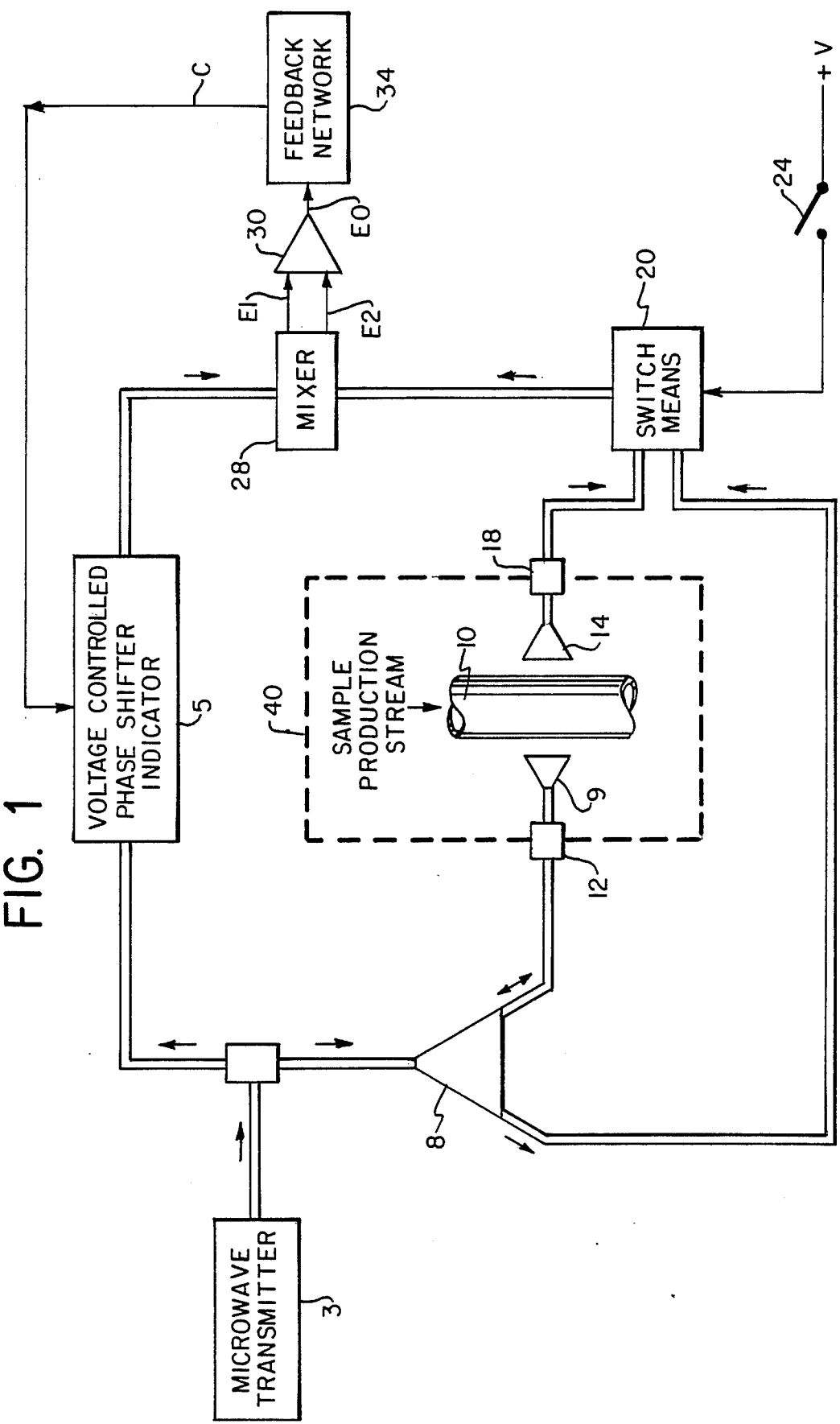
FIG. 1 is a combination simplified block diagram and a schematic of a watercut monitor constructed in accordance with the present invention.

The water cut monitor shown in FIG. 1 includes a microwave transmitter 3 providing electromagnetic energy, hereinafter referred to as microwave energy, at a microwave frequency. Transmitter 3 is low-powered and may use a microwave gun source. Transmitter 3 provides microwave energy to a conventional type voltage controlled phase shifter 5 and to a circulator 8. All conductance or carrying of microwave energy is accomplished by using conventional type waveguides.

Circulator 8 provides microwave energy from transmitter 3 to an antenna 9 which has an isolator 12 interconnecting antenna 9 to circulator 8. Antenna 9 transmits the microwave energy through a test cell 10 having windows 11 and 13 and having a sample stream of a fluid mixture passing through it. Windows 11 and 13 are made of a material that permits passage of microwave energy. The transmitted microwave energy passes through the fluid mixture and is received by antenna 11 which provides the received microwave energy to another isolator 18 which in turn provides the received microwave energy to a switch means 20.

The fluid mixture also reflects some of the microwave energy back to antenna 9 which passes back through antenna 9, isolator 12, to circulator 8. Circulator 8 blocks the reflected microwave energy from feeding back to transmitter 3 and provides the reflected microwave energy to switch means 20. Reflected microwave energy becomes more important as the distance between antennas 9 and 14 increases. This is especially true where a large pipeline carrying the fluid mixture is being monitored.

A positive direct current voltage $+V$ is provided to a switch 24 which is connected to switch means 20. With switch means 24 open, switch means 20 provides microwave energy from antenna 12 as a test microwave energy. When switch 24 is closed, the reflected microwave energy from circulator 8 is provided by switch means 20 as the test microwave energy.

The microwave energy from voltage control phase shifter 5, hereinafter called the reference microwave energy, and the test microwave energy from switch 20, are provided to a mixer 28 which mixes them to provide two electrical signals E1, E2, representative of the phases of the reference microwave energy and the test microwave energy.

A differential amplifier 30 provides an output signal E0 in accordance with the difference between signals E1 and E2. Signal E0 is a function of the phase difference between the reference microwave energy and the test microwave energy. Signal E0 may be applied to an indicator in which the amplitude of E0 will be representative of the phase difference or as shown in the present example may be provided to a feedback network 34. Feedback network 34 provides a control voltage C to voltage control phase shifter 5 controlling the phase of the reference microwave energy. Signal E0, and hence the control voltage C, decreases in amplitude until there is substantially 90° phase difference between the reference microwave energy and the test microwave energy. Voltage control phase shifter 5 indicates the amount of phase shift required to eliminate the phase difference.

Figure 2:
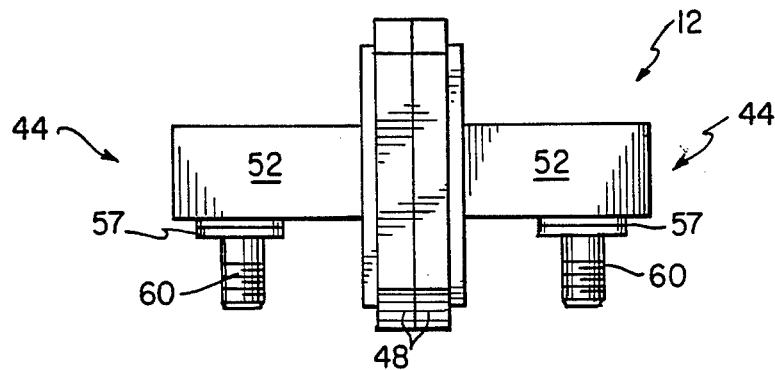
FIG. 2 shows the isolator of the present invention.

With reference to FIG. 2, there is shown isolator 12. Isolator 12 is used to protect an area adjacent test cell 10 from potential explosions. This unsafe area, which may be of any size, is shown in FIG. 1 by dashed line 40.

This unsafe area may be of any size and is shown in FIG. 1 by dashed line 40. The possibility of an explosion arises since many of the energy controlling components of the watercut monitor are made of metal for optimal microwave transmission. As such, all energy generated in the watercut circuits could be conducted to antennas 9 and 14. Under normal operating conditions, energy is limited to safe levels not capable of causing an explosion. In the event of accident or misuse of the watercut monitor much higher energy and energy of non-microwave frequencies could be applied to antennas 9 and 14.

Isolators 12 and 18 isolate antennas 9 and 14 from the buildup voltages that may occur on any of the other elements and thus protect them from arcing and causing an explosion.

Figure 3A:
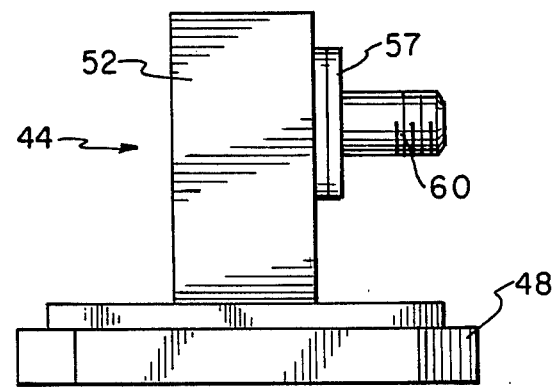
FIGS. 3A and 3B show one of the waveguides of the isolator.
Figure 3B:
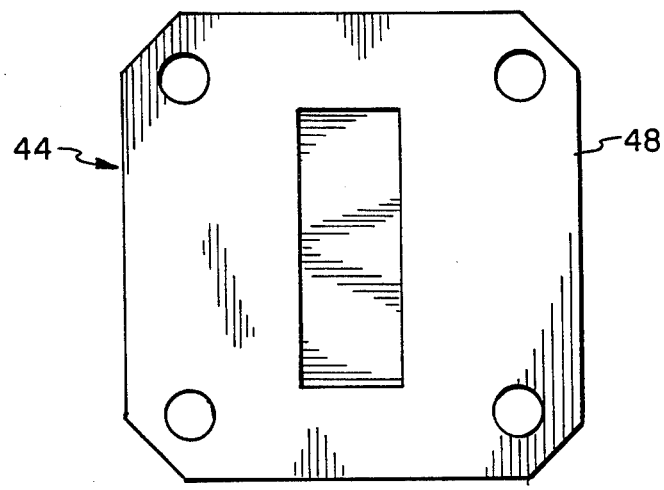

Isolator 12 is made up of two identical wave guides 44 which is shown in FIGS. 3A and 3B. Wave guides 44 include mounting flanges 48, a guide element 52, insulators 57 and a metal jack 60. Metal jack 60 is isolated from the wave guide 52 so that any voltage buildup on jack 60 does not appear on guide element 52. As can be seen in FIG. 3B, the RF energy aperture is identified by the numeral 65. It should be noted that although isolator 12 is shown with both jacks 60 facing downward it is obvious to one skilled in the art that one of the wave guides 44 may be reorientated 180° without loss of cross-sectional area of aperture 65, if it is so desired to do so.

The present invention has been described as being used with a water cut monitor of the type described and disclosed in U.S. Pat. No. 4,499,418, but it may also be used in either situation where a water cut monitor uses microwave energy singularly either as a direct pass through type of measurement or in another configuration as a reflected microwave energy configuration.

What is claimed is:

1. A petroleum stream microwave watercut monitor comprising:

test cell means for having a petroleum stream flowing through it while permitting microwave energy to enter the test cell means, source means for transmitting microwave energy, antenna means for irradiating the stream flowing in the test cell means with microwave energy and for receiving reflected microwave energy back from the stream in the test cell means, isolator means connected to the antenna means for passing microwave energy to and from the antenna means while isolating the antenna means from extraneous energies that may arise in the water cut monitor so as to prevent an accidental explosion due to those extraneous energies, circulating means connected to the source means and to the isolator means for providing the microwave energy from the source means to the antenna means through the isolator means and for providing reflected microwave energy from the antenna means by way of the isolator means to be provided as test microwave energy, and indicator means for providing an indication of the watercut of the petroleum stream in accordance with the phase difference between the transmitted microwave energy and the test microwave energy.

2. A monitor as described in claim 1 in which the indicator means further comprises:

a voltage controlled phase shifter receiving the transmitted microwave energy from said source means for phase shifting the transmitted microwave energy in accordance with a phase shift signal to provide a reference microwave energy and for providing an indication of the phase shift, and phase shift signal means receiving the reference microwave energy and the received microwave for providing the phase shift signal to the phase shifter until there is substantially a 90° phase difference between the reference microwave energy and the received microwave energy at which time the phase shifter's indicated phase shift corresponds to the water cut of the petroleum stream.

3. A monitor as described in claim 2 in which the phase shift signal means includes:

mixer means connected to the circulating means for mixing the reference microwave energy from the phase shifter with the microwave energy from the circulating means to provide two signals representative of the phases of the reference microwave energy and the microwave energy from the circulating means, a differential amplifier connected to the mixer means for providing an output signal in accordance with the difference between the two signals from the mixer means, and a feedback network connected to the phase shifter and to the differential amplifier which provides the phase shift signal in accordance with the output signal.

4. A monitor as described in claim 3 in which the isolator means includes:

first port means connected to the circulating means for conveying microwave to and from the circulating means, second port means connected to the antenna means for conveying microwave energy to and from the antenna means, first insulator means for providing electrical insulation, second insulator means for providing electrical insulation, and body means having an internal passageway and connected to the first and second port means and to the first and second insulator means in -a predetermined manner for conveying microwave energy from one port means to the other port means while providing isolation such that any extraneous energy appearing on one port means is not conducted to the other port means.

5. A petroleum stream microwave watercut monitor comprising:

test cell means for having a petroleum stream flowing through it while permitting microwave energy to pass through the test cell means, source means for transmitting microwave energy, first antenna means for irradiating the stream flowing in the test cell means with microwave energy, second antenna means for receiving microwave energy that has passed through the stream flowing in the test cell means to provide received microwave energy, first isolating means connecting the source means to the first antenna means for passing microwave energy to the first antenna means while isolating the first antenna means from extraneous energies that may arise in the water cut monitor so as to prevent an accidental explosion due to those extraneous energies, second isolating means connected to the second antenna means for passing received microwave energy from the second antenna means while isolating the second antenna means from extraneous energies that may arise in the water cut monitor so as to prevent an accidental explosion due to those extraneous energies, indicating means for providing an indication of the watercut of the petroleum stream in accordance with the phase difference between the transmitted microwave energy and the received microwave energy.

6. A monitor as described in claim 5 in which the indicator means further comprises:

a voltage controlled phase shifter receiving the transmitted microwave energy from said source means for phase shifting the transmitted microwave energy in accordance with phase shift signal to provide a reference microwave energy and for providing an indication of the above phase shift, and phase shift signal means receiving the reference microwave energy and the received microwave energy for providing the phase shift signal to the phase shifter until there is substantially a 90° phase difference between the reference microwave energy and the received microwave energy at which time the phase shifter's indicated phase shift corresponds to the water cut of the petroleum stream.

7. A monitor as described in claim 6 in which the phase shift signal means includes:

mixer means connected to the circulating means for mixing the reference microwave energy from the phase shifter with the received microwave energy to provide two signals representative of the phases of the reference microwave energy and the received microwave energy, and a differential amplifier connected to the mixer means for providing and output signal in accordance with the difference between the two signals from the mixer means, and a feedback network connected to the phase shifter and to the differential amplifier which provides the phase shift signal in accordance with the output signal.

8. A monitor is described in claim 7 in which each isolator means includes first port means for receiving microwave energy to and from the circulating means, second port means for providing microwave energy, first insulator means for providing electrical insulation, second insulator means for providing electrical insulation, and body means having an internal passageway and connected to the first and second port means and to the first and second insulator means in predetermined manner for conveying microwave energy from the first port means to the second port means while providing isolation such that any extraneous energy appearing on one port means is not conducted to the other port means.

* * * * *